US010175253B2

United States Patent
Flehmig

(10) Patent No.: US 10,175,253 B2
(45) Date of Patent: Jan. 8, 2019

(54) COMPILATION OF DETECTION REAGENTS, IN-VITRO METHOD FOR DETECTING MUTATED LEPTIN, AND USE OF A DETECTION REAGENT

(71) Applicant: Mediagnost Gesellschaft für Forschung und Herstellung von Diagnostika GmbH, Kusterdingen (DE)

(72) Inventor: Bertram Flehmig, Tubingen (DE)

(73) Assignee: MEDIAGNOST GESELLSCHAFT FÜR FORSCHUNG UND HERSTELLUNG VON DIAGNOSTIKA GMBH, Kusterdingen (DE)

( * ) Notice: Subject to any disclaimer, the term of this patent is extended or adjusted under 35 U.S.C. 154(b) by 0 days.

(21) Appl. No.: 15/558,322

(22) PCT Filed: Dec. 23, 2015

(86) PCT No.: PCT/EP2015/081186
§ 371 (c)(1),
(2) Date: Sep. 14, 2017

(87) PCT Pub. No.: WO2016/146221
PCT Pub. Date: Sep. 22, 2016

(65) Prior Publication Data
US 2018/0088134 A1    Mar. 29, 2018

(30) Foreign Application Priority Data
Mar. 16, 2015  (EP) .................................... 15159303

(51) Int. Cl.
*G01N 33/74*  (2006.01)
*C07K 14/575*  (2006.01)

(52) U.S. Cl.
CPC ......... *G01N 33/74* (2013.01); *C07K 14/5759* (2013.01); *G01N 2800/044* (2013.01)

(58) Field of Classification Search
None
See application file for complete search history.

(56) References Cited

PUBLICATIONS

Fischer-Posovszky et al.; "A New Missense Mutation in the Leptin Gene Causes Mild Obesity and Hypogonadism without Affecting T Cell Responsiveness"; J Clin Endocrinol Metab; 2010; pp. 2836-2840; vol. 95:6.
Funcke et al.; "Monogenic forms of childhood obesity due to mutations in the leptin gene"; Molecular and Cellular Pediatrics; 2014; pp. 1-8; vol. 1:3.
Kelesidis et al.; "Narrative Review: The Role of Leptin in Human Physiology: Emerging Clinical Applications"; Ann Intern Med.; 2010; pp. 93-100; vol. 152:2.
Kratzsch et al.; "A Rapid, Quantitative Immunofunctional Assay for Measuring Human Leptin"; Horm Res; 2000; pp. 127-132; vol. 57.
Lahlou et al.; "Soluble Leptin Receptor in Serum of Subjects With Complete Resistance to Leptin Relation to Fat Mass"; Diabetes; 2000; pp. 1347-1352; vol. 49.
Mazen et al.; "A novel homozygous missense mutation of the leptin gene (N103K) in an obese Egyptian patient"; Molecular Genetics and Metabolism; 2009; pp. 305-308; vol. 97.
Paz-Filho et al.; "Leptin treatment: Facts and expectations"; Metabolism Clinical and Experimental; 2014; pp. 1-11.
Wabitsch et al.; "Biologically Inactive Leptin and Early-Onset Extreme Obesity"; N Engl J Med; 2015; pp. 48-54; vol. 372.
Wu et al.; "Quantification of the Soluble Leptin Receptor in Human Blood by Ligand-Mediated Immunofunctional Assay"; J Clin Endocrinol Metab; 2002; pp. 2931-2939; vol. 87.

*Primary Examiner* — Lisa V Cook
(74) *Attorney, Agent, or Firm* — The Webb Law Firm

(57) ABSTRACT

The invention relates to a compilation of detection reagents, wherein the compilation comprises a first and a second detection reagent, wherein the first detection reagent binds non-mutated leptin with a first binding value, but does not bind mutated leptin or binds it with a maximum of 50% of the binding value of non-mutated leptin, and wherein the second detection reagent binds both mutated and non-mutated leptin with a second binding value. The invention furthermore relates to an in-vitro method for detecting mutated leptin and the use of a detection reagent.

19 Claims, 3 Drawing Sheets
Specification includes a Sequence Listing.

Figure 1a:
Leptin precursor (Homo sapiens)

```
  1 MHWGTLCGFL WLWPYLFYVQ AVPIQKVQDD TKTLIKTIVT RINDISHTQS VSSKQKVTGL  60
 61 DFIPGLHPIL TLSKMDQTLA VYQQILTSMP SRNVIQISND LENLRDLLHV LAFSKSCHLP 120
121 WASGLETLDS LGGVLEASGY STEVVALSRL QGSLQDMLWQ LDLSPGC              167
```

Figure 1b:
Leptin precursor variant D100Y (Homo sapiens)

```
  1 MHWGTLCGFL WLWPYLFYVQ AVPIQKVQDD TKTLIKTIVT RINDISHTQS VSSKQKVTGL  60
 61 DFIPGLHPIL TLSKMDQTLA VYQQILTSMP SRNVIQISNY LENLRDLLHV LAFSKSCHLP 120
121 WASGLETLDS LGGVLEASGY STEVVALSRL QGSLQDMLWQ LDLSPGC              167
```

Figure 1c:
Leptin precursor variant N103K (Homo sapiens)

```
  1 MHWGTLCGFL WLWPYLFYVQ AVPIQKVQDD TKTLIKTIVT RINDISHTQS VSSKQKVTGL  60
 61 DFIPGLHPIL TLSKMDQTLA VYQQILTSMP SRNVIQISND LEKLRDLLHV LAFSKSCHLP 120
121 WASGLETLDS LGGVLEASGY STEVVALSRL QGSLQDMLWQ LDLSPGC              167
```

Figure 1d:
Leptin precursor variant L72S (Homo sapiens)

```
  1 MHWGTLCGFL WLWPYLFYVQ AVPIQKVQDD TKTLIKTIVT RINDISHTQS VSSKQKVTGL  60
 61 DFIPGLHPIL TSSKMDQTLA VYQQILTSMP SRNVIQISND LENLRDLLHV LAFSKSCHLP 120
121 WASGLETLDS LGGVLEASGY STEVVALSRL QGSLQDMLWQ LDLSPGC              167
```

Figure 2a:
Leptin receptor isoform A (Homo sapiens)

```
  1 MICQKFCVVL LHWEFIYVIT AFNLSYPITP WRFKLSCMPP NSTYDYFLLP AGLSKNTSNS  60
 61 NGHYETAVEP KFNSSGTHFS NLSKTTFHCC FSEQDRNCS LCADNIEGKT FVSTVNSLVF 120
121 QQIDANWNIQ CWLKGDLKLF ICYVESLFKN LFRNYNYKVH LLYVLPEVLE DSPLVPQKGS 180
181 FQMVHCNCSV HECCECLVPV PTAKLNDTLL MCLKITSGGV IFQSPLMSVQ PINMVKPDPP 240
241 LGLHMEITDD GNLKISWSSP PLVPFPLQYQ VKYSENSTTV IREADKIVSA TSLLVDSILP 300
301 GSSYEVQVRG KRLDGPGIWS DWSTPRVFTT QDVIYFPPKI LTSVGSNVSF HCIYKKENKI 360
361 VPSKEIVWWM NLAEKIPQSQ YDVVSDHVSK VTFFNLNETK PRGKFTYDAV YCCNEHECHH 420
421 RYAELYVIDV NINISCETDG YLTKMTCRWS TSTIQSLAES TLQLRYHRSS LYCSDIPSIH 480
481 PISEPKDCYL QSDGFYECIF QPIFLLSGYT MWIRINHSLG SLDSPPTCVL PDSVVKPLPP 540
541 SSVKAEITIN IGLLKISWEK PVFPENNLQF QIRYGLSGKE VQWKMYEVYD AKSKSVSLPV 600
601 PDLCAVYAVQ VRCKRLDGLG YWSNWSNPAY TVVMDIKVPM RGPEFWRIIN GDTMKKEKNV 660
661 TLLWKPLMKN DSLCSVQRYV INHHTSCNGT WSEDVGNHTK FTPLWTEQAH TVTVLAINSI 720
721 GASVANFNLT FSWPMSKVNI VQSLSAYPLN SSCVIVSWIL SPSDYKLMYF IIEWKNLNED 780
781 GEIKWLRISS SVKKYYIHDH FIPIEKYQFS LYPIFMEQVG KPKIINSFTQ DDIEKHQSDA 840
841 GLYVIVPVII SSSILLLGTL LISHQRMKKL FWEDVPNPKN CSWAQGLNFQ KRTDIL     896
```

Figure 2b:
Leptin receptor isoform B (Homo sapiens)

```
  1 MICQKFCVVL LHWEFIYVIT AFNLSYPITP WRFKLSCMPP NSTYDYFLLP AGLSKNTSNS  60
 61 NGHYETAVEP KFNSSGTHFS NLSKTTFHCC FSEQDRNCS LCADNIEGKT FVSTVNSLVF 120
121 QQIDANWNIQ CWLKGDLKLF ICYVESLFKN LFRNYNYKVH LLYVLPEVLE DSPLVPQKGS 180
181 FQMVHCNCSV HECCECLVPV PTAKLNDTLL MCLKITSGGV IFQSPLMSVQ PINMVKPDPP 240
241 LGLHMEITDD GNLKISWSSP PLVPFPLQYQ VKYSENSTTV IREADKIVSA TSLLVDSILP 300
301 GSSYEVQVRG KRLDGPGIWS DWSTPRVFTT QDVIYFPPKI LTSVGSNVSF HCIYKKENKI 360
361 VPSKEIVWWM NLAEKIPQSQ YDVVSDHVSK VTFFNLNETK PRGKFTYDAV YCCNEHECHH 420
421 RYAELYVIDV NINISCETDG YLTKMTCRWS TSTIQSLAES TLQLRYHRSS LYCSDIPSIH 480
```

```
 481 PISEPKDCYL QSDGFYECIF QPIFLLSGYT MWIRINHSLG SLDSPPTCVL PDSVVKPLPP  540
 541 SSVKAEITIN IGLLKISWEK PVFPENNLQF QIRYGLSGKE VQWKMYEVYD AKSKSVSLPV  600
 601 PDLCAVYAVQ VRCKRLDGLG YWSNWSNPAY TVVMDIKVPM RGPEFWRIIN GDTMKKEKNV  660
 661 TLLWKPLMKN DSLCSVQRYV INHHTSCNGT WSEDVGNHTK FTFLWTEQAH TVTVLAINSI  720
 721 GASVANFNLT FSWPMSKVNI VQSLSAYPLN SSCVIVSWIL SPSDYKLMYF IIEWKNLNED  780
 781 GEIKWLRISS SVKKYYIHDH FIPIEKYQFS LYPIFMEGVG KPKIINSFTQ DDIEKHQSDA  840
 841 GLYVIVPVII SSSILLLGTL LISHQRMKKL FWEDVPNPKN CSWAQGLNFQ KPETFEHLFI  900
 901 KGTASVTCGP LLLEPETISE DISVDTSWKN KDEMMPTTVV SLLSTTDLEK GSVCISDQFN  960
 961 SVNFSEAEGT EVTYEDESQR QPFVKYATLI SNSKPSETGE EQGLINSSVT KCFSSKNSPL 1020
1021 KDSFSNSSWE IEAQAFFILS DQKPNIISPH LTFSEGLDEL LKLEGNFPEE NNDKKSIYYL 1080
1081 GVTSIKKRES QVLLTDKSEV SCPFPAPCLF TDIRVLQDSC SHFVENNINL GTSSKKTFAS 1140
1141 YMPQFQTCST QTHKIMENKM CDLTV                                      1165
```

Figure 2c:
Leptin receptor isoform C (Homo sapiens)

```
   1 MICQKFCVVL LHWEFIYVIT AFNLSYPITP WRFKLSCMPP NSTYDYFLLP AGLSKNTSNS   60
  61 NGHYETAVEP KFNSSGTHFS NLSKTTFHCC FRSEQDRNCS LCADNIEGKT FVSTVNSLVF  120
 121 QQIDANWNIQ CWLKGDLKLF ICYVESLPKN LFRNYNYKVH LLYVLPEVLE DSPLVPQKGS  180
 181 FQMVHCNCSV HECCECLVPV PTAKLNDTLL MCLKITSGGV IFQSPLMSVQ PINMVKPDPP  240
 241 LGLHMEITDD GNLKISWSSP PLVPFPLQYQ VKYSENSTTV IREADKIVSA TSLLVDSILP  300
 301 GSSYEVQVRG KRLDGPGIWS DWSTPRVFTT QDVIYFPPKI LTSVGSNVSF HCIYKKENKI  360
 361 VPSKEIVWWM NLAEKIPQSQ YDVVSDHVSK VTFFNLNETK PRGKFTYDAV YCCNEHECHH  420
 421 RYAELYVIDV NINISCETDG YLTKMTCRWS TSTIQSLAES TLQLRYHRSS LYCSDIPSIH  480
 481 PISEPKDCYL QSDGFYECIF QPIFLLSGYT MWIRINHSLG SLDSPPTCVL PDSVVKPLPP  540
 541 SSVKAEITIN IGLLKISWEK PVFPENNLQF QIRYGLSGKE VQWKMYEVYD AKSKSVSLPV  600
 601 PDLCAVYAVQ VRCKRLDGLG YWSNWSNPAY TVVMDIKVPM RGPEFWRIIN GDTMKKEKNV  660
 661 TLLWKPLMKN DSLCSVQRYV INHHTSCNGT WSEDVGNHTK FTFLWTEQAH TVTVLAINSI  720
 721 GASVANFNLT FSWPMSKVNI VQSLSAYPLN SSCVIVSWIL SPSDYKLMYF IIEWKNLNED  780
 781 GEIKWLRISS SVKKYYIHDH FIPIEKYQFS LYPIFMEGVG KPKIINSFTQ DDIEKHQSDA  840
 841 GLYVIVPVII SSSILLLGTL LISHQRMKKL FWEDVPNPKN CSWAQGLNFQ KMLEGSHFVK  900
 901 SHHHSLISST QGHKHCGRPQ GPLHRKTRDL CSLVYLLTLP PLLSYDPAKS PSVRNTQE    958
```

Figure 2d:
Leptin receptor isoform D (Homo sapiens)

```
   1 MICQKFCVVL LHWEFIYVIT AFNLSYPITP WRFKLSCMPP NSTYDYFLLP AGLSKNTSNS   60
  61 NGHYETAVEP KFNSSGTHFS NLSKTTFHCC FRSEQDRNCS LCADNIEGKT FVSTVNSLVF  120
 121 QQIDANWNIQ CWLKGDLKLF ICYVESLPKN LFRNYNYKVH LLYVLPEVLE DSPLVPQKGS  180
 181 FQMVHCNCSV HECCECLVPV PTAKLNDTLL MCLKITSGGV IFQSPLMSVQ PINMVKPDPP  240
 241 LGLHMEITDD GNLKISWSSP PLVPFPLQYQ VKYSENSTTV IREADKIVSA TSLLVDSILP  300
 301 GSSYEVQVRG KRLDGPGIWS DWSTPRVFTT QDVIYFPPKI LTSVGSNVSF HCIYKKENKI  360
 361 VPSKEIVWWM NLAEKIPQSQ YDVVSDHVSK VTFFNLNETK PRGKFTYDAV YCCNEHECHH  420
 421 RYAELYVIDV NINISCETDG YLTKMTCRWS TSTIQSLAES TLQLRYHRSS LYCSDIPSIH  480
 481 PISEPKDCYL QSDGFYECIF QPIFLLSGYT MWIRINHSLG SLDSPPTCVL PDSVVKPLPP  540
 541 SSVKAEITIN IGLLKISWEK PVFPENNLQF QIRYGLSGKE VQWKMYEVYD AKSKSVSLPV  600
 601 PDLCAVYAVQ VRCKRLDGLG YWSNWSNPAY TVVMDIKVPM RGPEFWRIIN GDTMKKEKNV  660
 661 TLLWKPLMKN DSLCSVQRYV INHHTSCNGT WSEDVGNHTK FTFLWTEQAH TVTVLAINSI  720
 721 GASVANFNLT FSWPMSKVNI VQSLSAYPLN SSCVIVSWIL SPSDYKLMYF IIEWKNLNED  780
 781 GEIKWLRISS SVKKYYIHDH FIPIEKYQFS LYPIFMEGVG KPKIINSFTQ DDIEKHQSDA  840
 841 GLYVIVPVII SSSILLLGTL LISHQRMKKL FWEDVPNPKN CSWAQGLNFQ KKMPGTKELL  900
 901 QGGWLT                                                             906
```

Figure 2e:
Leptin receptor isoform E (Homo sapiens)

```
   1 MICQKFCVVL LHWEFIYVIT AFNLSYPITP WRFKLSCMPP NSTYDYFLLP AGLSKNTSNS   60
  61 NGHYETAVEP KFNSSGTHFS NLSKTTFHCC FRSEQDRNCS LCADNIEGKT FVSTVNSLVF  120
 121 QQIDANWNIQ CWLKGDLKLF ICYVESLPKN LFRNYNYKVH LLYVLPEVLE DSPLVPQKGS  180
 181 FQMVHCNCSV HECCECLVPV PTAKLNDTLL MCLKITSGGV IFQSPLMSVQ PINMVKPDPP  240
```

```
241 LGLHMEITDD DGNLKISWSSP PLVPFPLQYQ VKYSENSTTV IREADKIVSA TSLLVDSILP 300
301 GSSYEVQVRG KRLDGPGIWS DWSTPRVFTT QDVIYFPPKI LTSVGSNVSF HCIYKKENKI 360
361 VPSKEIVWWM NLAEKIPQSQ YDVVSDHVSK VTFFNLNETK PRGKFTYDAV YCCNEHECHH 420
421 RYAELYVIDV NINISCETDG YLTKMTCRWS TSTIQSLAES TLQLRYHRSS LYCSDIPSIH 480
481 PISEPKDCYL QSDGFYECIF QPIFLLSGYT MWIRINHSLG SLDSPPTCVL PDSVVKPLPP 540
541 SSVKAEITIN IGLLKISWEK PVFPENNLQF QIRYGLSGKE VQWKMYEVYD AKSKSVSLPV 600
601 PDLCAVYAVQ VRCKRLDGLG YWSNWSNPAY TVVMDIKVPM RGPEFWRIIN GDTMKKEKNV 660
661 TLLWKPLMKN DSLCSVQRYV INHHRTSCNGT WSEDVGNHTK FTFLWTEQAH YVTVLAINSI 720
721 GASVANFNLT FSWPMSKVNI VQSLSAYPLN SSCVIVSWIL SPSDYKLMYF IIEWKNLNED 780
781 GEIKWLRISS SVKKYYIHDH FIPIEKYQFS LYPIFMEGVG KPKIINSFTQ DDIEKHQSD  839
```

Figure 2f:

Leptin receptor isoform B fragment Thr20 - Asp839 (Homo sapiens)

```
  1 TAFNLSYPIT PWRPKLSCMP PNSTYDYFLL PAGLSKNTSN SNGHYETAVE PKFNSSGTHF  60
 61 SNLSKTTFHC CFRSEQDRNC SLCADNIEGK TFVSTVNSLV FQQIDANWNI QCWLKGDLKL 120
121 FICYVESLFK NLFRNYNYKV HLLYVLPEVL EDSPLVPQKG SFQMVHCNCS VHECCECLVP 180
181 VPTAKLNDTL LMCLKITSGG VIFQSPLMSV QPINMVKPDP PLGLHMEITD DGNLKISWSS 240
241 PPLVPFPLQY QVKYSENSTT VIREADKIVS ATSLLVDSIL PGSSYEVQVR GKRLDGPGIW 300
301 SDWSTPRVFT TQDVIYFPPK ILTSVGSNVS FHCIYKKENK IVPSKEIVWW MNLAEKIPQS 360
361 QYDVVSDHVS KVTFFNLNET KPRGKFTYDA VYCCNEHECH HRYAELYVID VNINISCETD 420
421 GYLTKMTCRW STSTIQSLAE STLQLRYHRS SLYCSDIPSI HPISEPKDCY LQSDGFYECI 480
481 FQPIFLLSGY TMWIRINHSL GSLDSPPTCV LPDSVVKPLP PSSVKAEITI NIGLLKISWE 540
541 KPVFPENNLQ FQIRYGLSGK EVQWKMYEVY DAKSKSVSLP VPDLCAVYAV QVRCKRLDGL 600
601 GYWSNWSNPA YTVVMDIKVP MRGPEFWRII NGDTMKKEKN VTLLWKPLMK NDSLCSVQRY 660
661 VINHHRTSCNG TWSEDVGNHT KFTFLWTEQA HYVTVLAINS IGASVANFNL TFSWPMSKVN 720
721 IVQSLSAYPL NSSCVIVSWI LSPSDYKLMY FIIEWKNLNE DGEIKWLRIS SSVKKYYIHD 780
781 HFIPIEKYQF SLYPIFMEGV GKPKIINSFT QDDIEKHQSD                      820
``` ial application No. 15159303.5, filed Mar. 16, 2015, the

SEQUENCE LISTING

<160> NUMBER OF SEQ ID NOS: 10

<210> SEQ ID NO 1
<211> LENGTH: 167
<212> TYPE: PRT
<213> ORGANISM: Homo sapiens

<400> SEQUENCE: 1

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 2
<211> LENGTH: 167
<212> TYPE: PRT
<213> ORGANISM: Homo sapiens

<400> SEQUENCE: 2

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Tyr Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 3
<211> LENGTH: 167
<212> TYPE: PRT
<213> ORGANISM: Homo sapiens

<400> SEQUENCE: 3

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Lys Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 4
<211> LENGTH: 167
<212> TYPE: PRT
<213> ORGANISM: Homo sapiens

<400> SEQUENCE: 4

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Ser Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

```
Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 5
<211> LENGTH: 896
<212> TYPE: PRT
<213> ORGANISM: Homo sapiens

<400> SEQUENCE: 5

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335
```

```
Pro Pro Lys Ile Leu Thr Ser Val Gly Ser Asn Val Ser Phe His Cys
            340                 345                 350
Ile Tyr Lys Lys Glu Asn Lys Ile Val Pro Ser Lys Glu Ile Val Trp
            355                 360                 365
Trp Met Asn Leu Ala Glu Lys Ile Pro Gln Ser Gln Tyr Asp Val Val
    370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                405                 410                 415
Glu Cys His His Arg Tyr Ala Glu Leu Tyr Val Ile Asp Val Asn Ile
            420                 425                 430
Asn Ile Ser Cys Glu Thr Asp Gly Tyr Leu Thr Lys Met Thr Cys Arg
            435                 440                 445
Trp Ser Thr Ser Thr Ile Gln Ser Leu Ala Glu Ser Thr Leu Gln Leu
    450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                485                 490                 495
Glu Cys Ile Phe Gln Pro Ile Phe Leu Leu Ser Gly Tyr Thr Met Trp
            500                 505                 510
Ile Arg Ile Asn His Ser Leu Gly Ser Leu Asp Ser Pro Pro Thr Cys
            515                 520                 525
Val Leu Pro Asp Ser Val Val Lys Pro Leu Pro Pro Ser Ser Val Lys
    530                 535                 540
Ala Glu Ile Thr Ile Asn Ile Gly Leu Leu Lys Ile Ser Trp Glu Lys
545                 550                 555                 560
Pro Val Phe Pro Glu Asn Asn Leu Gln Phe Gln Ile Arg Tyr Gly Leu
                565                 570                 575
Ser Gly Lys Glu Val Gln Trp Lys Met Tyr Glu Val Tyr Asp Ala Lys
            580                 585                 590
Ser Lys Ser Val Ser Leu Pro Val Pro Asp Leu Cys Ala Val Tyr Ala
            595                 600                 605
Val Gln Val Arg Cys Lys Arg Leu Asp Gly Leu Gly Tyr Trp Ser Asn
    610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                645                 650                 655
Glu Lys Asn Val Thr Leu Leu Trp Lys Pro Leu Met Lys Asn Asp Ser
            660                 665                 670
Leu Cys Ser Val Gln Arg Tyr Val Ile Asn His His Thr Ser Cys Asn
            675                 680                 685
Gly Thr Trp Ser Glu Asp Val Gly Asn His Thr Lys Phe Thr Phe Leu
    690                 695                 700
Trp Thr Glu Gln Ala His Thr Val Thr Val Leu Ala Ile Asn Ser Ile
705                 710                 715                 720
Gly Ala Ser Val Ala Asn Phe Asn Leu Thr Phe Ser Trp Pro Met Ser
                725                 730                 735
Lys Val Asn Ile Val Gln Ser Leu Ser Ala Tyr Pro Leu Asn Ser Ser
            740                 745                 750
```

```
Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
    770                 775                 780

Trp Leu Arg Ile Ser Ser Val Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
                820                 825                 830

Ile Glu Lys His Gln Ser Asp Ala Gly Leu Tyr Val Ile Val Pro Val
            835                 840                 845

Ile Ile Ser Ser Ser Ile Leu Leu Leu Gly Thr Leu Leu Ile Ser His
            850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Arg Thr Asp Ile Leu
                885                 890                 895

<210> SEQ ID NO 6
<211> LENGTH: 1165
<212> TYPE: PRT
<213> ORGANISM: Homo sapiens

<400> SEQUENCE: 6

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240
```

-continued

Leu Gly Leu His Met Glu Ile Thr Asp Asp Gly Asn Leu Lys Ile Ser
                245                 250                 255
Trp Ser Ser Pro Pro Leu Val Pro Phe Pro Leu Gln Tyr Gln Val Lys
            260                 265                 270
Tyr Ser Glu Asn Ser Thr Thr Val Ile Arg Glu Ala Asp Lys Ile Val
        275                 280                 285
Ser Ala Thr Ser Leu Leu Val Asp Ser Ile Leu Pro Gly Ser Ser Tyr
    290                 295                 300
Glu Val Gln Val Arg Gly Lys Arg Leu Asp Pro Gly Ile Trp Ser
305                 310                 315                 320
Asp Trp Ser Thr Pro Arg Val Phe Thr Thr Gln Asp Val Ile Tyr Phe
                325                 330                 335
Pro Pro Lys Ile Leu Thr Ser Val Gly Ser Asn Val Ser Phe His Cys
            340                 345                 350
Ile Tyr Lys Lys Glu Asn Lys Ile Val Pro Ser Lys Glu Ile Val Trp
        355                 360                 365
Trp Met Asn Leu Ala Glu Lys Ile Pro Gln Ser Gln Tyr Asp Val Val
    370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                405                 410                 415
Glu Cys His His Arg Tyr Ala Glu Leu Tyr Val Ile Asp Val Asn Ile
            420                 425                 430
Asn Ile Ser Cys Glu Thr Asp Gly Tyr Leu Thr Lys Met Thr Cys Arg
        435                 440                 445
Trp Ser Thr Ser Thr Ile Gln Ser Leu Ala Glu Ser Thr Leu Gln Leu
    450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                485                 490                 495
Glu Cys Ile Phe Gln Pro Ile Phe Leu Leu Ser Gly Tyr Thr Met Trp
            500                 505                 510
Ile Arg Ile Asn His Ser Leu Gly Ser Leu Asp Ser Pro Pro Thr Cys
        515                 520                 525
Val Leu Pro Asp Ser Val Val Lys Pro Leu Pro Pro Ser Ser Val Lys
    530                 535                 540
Ala Glu Ile Thr Ile Asn Ile Gly Leu Leu Lys Ile Ser Trp Glu Lys
545                 550                 555                 560
Pro Val Phe Pro Glu Asn Asn Leu Gln Phe Gln Ile Arg Tyr Gly Leu
                565                 570                 575
Ser Gly Lys Glu Val Gln Trp Lys Met Tyr Glu Val Tyr Asp Ala Lys
            580                 585                 590
Ser Lys Ser Val Ser Leu Pro Val Pro Asp Leu Cys Ala Val Tyr Ala
        595                 600                 605
Val Gln Val Arg Cys Lys Arg Leu Asp Gly Leu Gly Tyr Trp Ser Asn
    610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                645                 650                 655

-continued

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
            675                 680                 685

Gly Thr Trp Ser Glu Asp Val Gly Asn His Thr Lys Phe Thr Phe Leu
            690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
            725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
            770                 775                 780

Trp Leu Arg Ile Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
            805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
            835                 840                 845

Ile Ile Ser Ser Ser Ile Leu Leu Leu Gly Thr Leu Leu Ile Ser His
            850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
            885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
            915                 920                 925

Lys Asn Lys Asp Glu Met Met Pro Thr Thr Val Val Ser Leu Leu Ser
            930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Asp
            965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu Glu Gln Gly Leu Ile Asn Ser Ser
            995                 1000                1005

Val Thr Lys Cys Phe Ser Ser Lys Asn Ser Pro Leu Lys Asp Ser
            1010                1015                1020

Phe Ser Asn Ser Ser Trp Glu Ile Glu Ala Gln Ala Phe Phe Ile
            1025                1030                1035

Leu Ser Asp Gln His Pro Asn Ile Ile Ser Pro His Leu Thr Phe
            1040                1045                1050

Ser Glu Gly Leu Asp Glu Leu Leu Lys Leu Glu Gly Asn Phe Pro
            1055                1060                1065

```
Glu Glu Asn Asn Asp Lys Lys Ser Ile Tyr Tyr Leu Gly Val Thr
    1070            1075                1080

Ser Ile Lys Lys Arg Glu Ser Gly Val Leu Leu Thr Asp Lys Ser
    1085            1090                1095

Arg Val Ser Cys Pro Phe Pro Ala Pro Cys Leu Phe Thr Asp Ile
    1100            1105                1110

Arg Val Leu Gln Asp Ser Cys Ser His Phe Val Glu Asn Asn Ile
    1115            1120                1125

Asn Leu Gly Thr Ser Ser Lys Lys Thr Phe Ala Ser Tyr Met Pro
    1130            1135                1140

Gln Phe Gln Thr Cys Ser Thr Gln Thr His Lys Ile Met Glu Asn
    1145            1150                1155

Lys Met Cys Asp Leu Thr Val
    1160            1165

<210> SEQ ID NO 7
<211> LENGTH: 958
<212> TYPE: PRT
<213> ORGANISM: Homo sapiens

<400> SEQUENCE: 7

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270
```

```
Tyr Ser Glu Asn Ser Thr Thr Val Ile Arg Glu Ala Asp Lys Ile Val
            275                 280                 285

Ser Ala Thr Ser Leu Leu Val Asp Ser Ile Leu Pro Gly Ser Ser Tyr
        290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
        370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
        450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685
```

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
            725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
        770                 775                 780

Trp Leu Arg Ile Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
            805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
    850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Met Leu Glu Gly Ser
            885                 890                 895

Met Phe Val Lys Ser His His His Ser Leu Ile Ser Ser Thr Gln Gly
            900                 905                 910

His Lys His Cys Gly Arg Pro Gln Gly Pro Leu His Arg Lys Thr Arg
        915                 920                 925

Asp Leu Cys Ser Leu Val Tyr Leu Leu Thr Leu Pro Pro Leu Leu Ser
    930                 935                 940

Tyr Asp Pro Ala Lys Ser Pro Ser Val Arg Asn Thr Gln Glu
945                 950                 955

<210> SEQ ID NO 8
<211> LENGTH: 906
<212> TYPE: PRT
<213> ORGANISM: Homo sapiens

<400> SEQUENCE: 8

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

```
Ser Thr Val Asn Ser Leu Val Phe Gln Gln Ile Asp Ala Asn Trp Asn
            115                 120                 125

Ile Gln Cys Trp Leu Lys Gly Asp Leu Lys Leu Phe Ile Cys Tyr Val
130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
195                 200                 205

Leu Leu Met Cys Leu Lys Ile Thr Ser Gly Gly Val Ile Phe Gln Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
            245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
275                 280                 285

Ser Ala Thr Ser Leu Leu Val Asp Ser Ile Leu Pro Gly Ser Ser Tyr
290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
            325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
            355                 360                 365

Trp Met Asn Leu Ala Glu Lys Ile Pro Gln Ser Gln Tyr Asp Val Val
370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
            405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
            435                 440                 445

Trp Ser Thr Ser Thr Ile Gln Ser Leu Ala Glu Ser Thr Leu Gln Leu
450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
            485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
            515                 520                 525
```

```
Val Leu Pro Asp Ser Val Val Lys Pro Leu Pro Pro Ser Ser Val Lys
            530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Lys Met Pro Gly Thr
                885                 890                 895

Lys Glu Leu Leu Gly Gly Trp Leu Thr
            900                 905

<210> SEQ ID NO 9
<211> LENGTH: 839
<212> TYPE: PRT
<213> ORGANISM: Homo sapiens
```

<400> SEQUENCE: 9

```
Met Ile Cys Gln Lys Phe Cys Val Val Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
            35                  40                  45

Leu Pro Ala Gly Leu Ser Lys Asn Thr Ser Asn Ser Asn Gly His Tyr
        50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415
```

```
Glu Cys His His Arg Tyr Ala Glu Leu Tyr Val Ile Asp Val Asn Ile
                420                 425                 430
Asn Ile Ser Cys Glu Thr Asp Gly Tyr Leu Thr Lys Met Thr Cys Arg
            435                 440                 445
Trp Ser Thr Ser Thr Ile Gln Ser Leu Ala Glu Ser Thr Leu Gln Leu
450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                485                 490                 495
Glu Cys Ile Phe Gln Pro Ile Phe Leu Leu Ser Gly Tyr Thr Met Trp
                500                 505                 510
Ile Arg Ile Asn His Ser Leu Gly Ser Leu Asp Ser Pro Pro Thr Cys
                515                 520                 525
Val Leu Pro Asp Ser Val Val Lys Pro Leu Pro Pro Ser Ser Val Lys
                530                 535                 540
Ala Glu Ile Thr Ile Asn Ile Gly Leu Leu Lys Ile Ser Trp Glu Lys
545                 550                 555                 560
Pro Val Phe Pro Glu Asn Asn Leu Gln Phe Gln Ile Arg Tyr Gly Leu
                565                 570                 575
Ser Gly Lys Glu Val Gln Trp Lys Met Tyr Glu Val Tyr Asp Ala Lys
                580                 585                 590
Ser Lys Ser Val Ser Leu Pro Val Pro Asp Leu Cys Ala Val Tyr Ala
                595                 600                 605
Val Gln Val Arg Cys Lys Arg Leu Asp Gly Leu Gly Tyr Trp Ser Asn
                610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                645                 650                 655
Glu Lys Asn Val Thr Leu Leu Trp Lys Pro Leu Met Lys Asn Asp Ser
                660                 665                 670
Leu Cys Ser Val Gln Arg Tyr Val Ile Asn His His Thr Ser Cys Asn
                675                 680                 685
Gly Thr Trp Ser Glu Asp Val Gly Asn His Thr Lys Phe Thr Phe Leu
                690                 695                 700
Trp Thr Glu Gln Ala His Thr Val Thr Val Leu Ala Ile Asn Ser Ile
705                 710                 715                 720
Gly Ala Ser Val Ala Asn Phe Asn Leu Thr Phe Ser Trp Pro Met Ser
                725                 730                 735
Lys Val Asn Ile Val Gln Ser Leu Ser Ala Tyr Pro Leu Asn Ser Ser
                740                 745                 750
Cys Val Ile Val Ser Trp Ile Leu Ser Pro Ser Asp Tyr Lys Leu Met
                755                 760                 765
Tyr Phe Ile Ile Glu Trp Lys Asn Leu Asn Glu Asp Gly Glu Ile Lys
                770                 775                 780
Trp Leu Arg Ile Ser Ser Ser Val Lys Lys Tyr Tyr Ile His Asp His
785                 790                 795                 800
Phe Ile Pro Ile Glu Lys Tyr Gln Phe Ser Leu Tyr Pro Ile Phe Met
                805                 810                 815
```

```
Glu Gly Val Gly Lys Pro Lys Ile Ile Asn Ser Phe Thr Gln Asp Asp
                820                 825                 830

Ile Glu Lys His Gln Ser Asp
        835

<210> SEQ ID NO 10
<211> LENGTH: 820
<212> TYPE: PRT
<213> ORGANISM: Homo sapiens

<400> SEQUENCE: 10

Thr Ala Phe Asn Leu Ser Tyr Pro Ile Thr Pro Trp Arg Phe Lys Leu
1               5                   10                  15

Ser Cys Met Pro Pro Asn Ser Thr Tyr Asp Tyr Phe Leu Leu Pro Ala
            20                  25                  30

Gly Leu Ser Lys Asn Thr Ser Asn Ser Asn Gly His Tyr Glu Thr Ala
        35                  40                  45

Val Glu Pro Lys Phe Asn Ser Ser Gly Thr His Phe Ser Asn Leu Ser
    50                  55                  60

Lys Thr Thr Phe His Cys Cys Phe Arg Ser Glu Gln Asp Arg Asn Cys
65                  70                  75                  80

Ser Leu Cys Ala Asp Asn Ile Glu Gly Lys Thr Phe Val Ser Thr Val
                85                  90                  95

Asn Ser Leu Val Phe Gln Gln Ile Asp Ala Asn Trp Asn Ile Gln Cys
            100                 105                 110

Trp Leu Lys Gly Asp Leu Lys Leu Phe Ile Cys Tyr Val Glu Ser Leu
        115                 120                 125

Phe Lys Asn Leu Phe Arg Asn Tyr Asn Tyr Lys Val His Leu Leu Tyr
    130                 135                 140

Val Leu Pro Glu Val Leu Glu Asp Ser Pro Leu Val Pro Gln Lys Gly
145                 150                 155                 160

Ser Phe Gln Met Val His Cys Asn Cys Ser Val His Glu Cys Cys Glu
                165                 170                 175

Cys Leu Val Pro Val Pro Thr Ala Lys Leu Asn Asp Thr Leu Leu Met
            180                 185                 190

Cys Leu Lys Ile Thr Ser Gly Gly Val Ile Phe Gln Ser Pro Leu Met
        195                 200                 205

Ser Val Gln Pro Ile Asn Met Val Lys Pro Asp Pro Pro Leu Gly Leu
    210                 215                 220

His Met Glu Ile Thr Asp Asp Gly Asn Leu Lys Ile Ser Trp Ser Ser
225                 230                 235                 240

Pro Pro Leu Val Pro Phe Pro Leu Gln Tyr Gln Val Lys Tyr Ser Glu
                245                 250                 255

Asn Ser Thr Thr Val Ile Arg Glu Ala Asp Lys Ile Val Ser Ala Thr
            260                 265                 270

Ser Leu Leu Val Asp Ser Ile Leu Pro Gly Ser Ser Tyr Glu Val Gln
        275                 280                 285

Val Arg Gly Lys Arg Leu Asp Gly Pro Gly Ile Trp Ser Asp Trp Ser
    290                 295                 300

Thr Pro Arg Val Phe Thr Thr Gln Asp Val Ile Tyr Phe Pro Pro Lys
305                 310                 315                 320

Ile Leu Thr Ser Val Gly Ser Asn Val Ser Phe His Cys Ile Tyr Lys
                325                 330                 335

Lys Glu Asn Lys Ile Val Pro Ser Lys Glu Ile Val Trp Trp Met Asn
            340                 345                 350
```

-continued

```
Leu Ala Glu Lys Ile Pro Gln Ser Gln Tyr Asp Val Ser Asp His
        355                 360                 365
Val Ser Lys Val Thr Phe Phe Asn Leu Asn Glu Thr Lys Pro Arg Gly
    370                 375                 380
Lys Phe Thr Tyr Asp Ala Val Tyr Cys Cys Asn Glu His Glu Cys His
385                 390                 395                 400
His Arg Tyr Ala Glu Leu Tyr Val Ile Asp Val Asn Ile Asn Ile Ser
                405                 410                 415
Cys Glu Thr Asp Gly Tyr Leu Thr Lys Met Thr Cys Arg Trp Ser Thr
                420                 425                 430
Ser Thr Ile Gln Ser Leu Ala Glu Ser Thr Leu Gln Leu Arg Tyr His
        435                 440                 445
Arg Ser Ser Leu Tyr Cys Ser Asp Ile Pro Ser Ile His Pro Ile Ser
    450                 455                 460
Glu Pro Lys Asp Cys Tyr Leu Gln Ser Asp Gly Phe Tyr Glu Cys Ile
465                 470                 475                 480
Phe Gln Pro Ile Phe Leu Leu Ser Gly Tyr Thr Met Trp Ile Arg Ile
                485                 490                 495
Asn His Ser Leu Gly Ser Leu Asp Ser Pro Thr Cys Val Leu Pro
                500                 505                 510
Asp Ser Val Val Lys Pro Leu Pro Ser Ser Val Lys Ala Glu Ile
    515                 520                 525
Thr Ile Asn Ile Gly Leu Leu Lys Ile Ser Trp Glu Lys Pro Val Phe
                530                 535                 540
Pro Glu Asn Asn Leu Gln Phe Gln Ile Arg Tyr Gly Leu Ser Gly Lys
545                 550                 555                 560
Glu Val Gln Trp Lys Met Tyr Glu Val Tyr Asp Ala Lys Ser Lys Ser
                565                 570                 575
Val Ser Leu Pro Val Pro Asp Leu Cys Ala Val Tyr Ala Val Gln Val
        580                 585                 590
Arg Cys Lys Arg Leu Asp Gly Leu Gly Tyr Trp Ser Asn Trp Ser Asn
    595                 600                 605
Pro Ala Tyr Thr Val Val Met Asp Ile Lys Val Pro Met Arg Gly Pro
610                 615                 620
Glu Phe Trp Arg Ile Ile Asn Gly Asp Thr Met Lys Lys Glu Lys Asn
625                 630                 635                 640
Val Thr Leu Leu Trp Lys Pro Leu Met Lys Asn Asp Ser Leu Cys Ser
                645                 650                 655
Val Gln Arg Tyr Val Ile Asn His His Thr Ser Cys Asn Gly Thr Trp
            660                 665                 670
Ser Glu Asp Val Gly Asn His Thr Lys Phe Thr Phe Leu Trp Thr Glu
            675                 680                 685
Gln Ala His Thr Val Thr Val Leu Ala Ile Asn Ser Ile Gly Ala Ser
        690                 695                 700
Val Ala Asn Phe Asn Leu Thr Phe Ser Trp Pro Met Ser Lys Val Asn
705                 710                 715                 720
Ile Val Gln Ser Leu Ser Ala Tyr Pro Leu Asn Ser Ser Cys Val Ile
                725                 730                 735
Val Ser Trp Ile Leu Ser Pro Ser Asp Tyr Lys Leu Met Tyr Phe Ile
                740                 745                 750
Ile Glu Trp Lys Asn Leu Asn Glu Asp Gly Glu Ile Lys Trp Leu Arg
                755                 760                 765
```

-continued

```
Ile Ser Ser Ser Val Lys Lys Tyr Tyr Ile His Asp His Phe Ile Pro
    770             775             780
Ile Glu Lys Tyr Gln Phe Ser Leu Tyr Pro Ile Phe Met Glu Gly Val
785             790             795             800
Gly Lys Pro Lys Ile Ile Asn Ser Phe Thr Gln Asp Asp Ile Glu Lys
            805             810             815
His Gln Ser Asp
        820
```

COMPILATION OF DETECTION REAGENTS, IN-VITRO METHOD FOR DETECTING MUTATED LEPTIN, AND USE OF A DETECTION REAGENT

CROSS-REFERENCE TO RELATED APPLICATIONS

This application is the United States national phase of PCT International Application No. PCT/EP2015/081186 filed Dec. 23, 2015, which claims priority to European Patent Application No. 15159303.5, filed Mar. 16, 2015, the disclosures of each of which are hereby incorporated by reference in their entireties.

The Sequence Listing associated with this application is filed in electronic format via EFS-Web and is hereby incorporated by reference into the specification in its entirety. The name of the text file containing the Sequence Listing is 1706260_ST25.txt. The size of the text file is 54,377 bytes, and the text file was created on Sep. 12, 2017.

BACKGROUND OF THE INVENTION

Field of the Invention

The present invention relates to a compilation of detection reagents, an in-vitro method for detecting mutated leptin and the use of a detection reagent which binds non-mutated leptin, but does not bind mutated leptin or binds it with a maximum of 50% of the binding value of non-mutated leptin, in the diagnosis, in particular in the differential diagnosis, of obesity.

Obesity, which is also referred to as adiposity, is a nutritional and metabolic disease in which the individuals affected are considerably overweight. The excess weight is to be attributed in particular to the formation of body fat. The main component of adipose tissue is adipocytes, wherein a distinction is made between univacuolar adipocytes and plurivacuolar adipocytes.

Univacuolar adipocytes have only one vacuole filled with lipids. This cell type makes up the so-called white adipose tissue. In the case of plurivacuolar adipocytes, the lipids are stored in several vacuoles separated from each other. Plurivacuolar adipocytes primarily make up the so-called brown adipose tissue.

Adipocytes contain the obesity gene which encodes leptin. Leptin is also produced in smaller quantities in the placenta, the stomach lining, the bone marrow, the breast epithelium, the skeletal muscles, the pituitary gland and the hypothalamus.

Leptin inhibits the occurrence of feelings of hunger and plays an important role in the regulation of lipid metabolism in mammals, in particular humans. Leptin is primarily secreted by the adipocytes of the white adipose tissue. The leptin level is positively correlated with the amount of body fat.

Human leptin is a protein which is made up of 167 amino acids including signal peptide. The N-terminal signal peptide has a length of 21 amino acids and is cleaved off during the secretion process, with the result that the mature leptin contains 146 amino acids. Leptin acts by binding to specific leptin receptors which are present both in the brain and in peripheral tissues. Because of alternative splicing processes, there are several isoforms of the leptin receptor. Isoform A is a short leptin receptor isoform and plays an important role in the transport of leptin across the blood-brain barrier. Isoform B, which is the so-called long leptin isoform, brings about signal transduction and is expressed in the hypothalamus.

During binding of leptin to isoform B of the leptin receptor, several signal transduction pathways, including Janus kinase (JAK) and STAT (Signal Transducers and Activators of Transcription) proteins, in particular STAT-3, and phosphatidylinositol 3-kinase (PI3K), are activated. In other signaling pathways, mitogen-activated protein kinase (MAPK), 5' adenosine monophosphate-activated protein kinase (AMPK) and the mechanistic, or mammalian, target of rapamycin (mTOR) are activated.

Homozygous mutations in the leptin gene lead to a complete leptin deficiency, as is described in extremely rare cases of human obesity.

By far the larger majority of obese humans, however, have high circulating leptin levels (Kelesidis T. et al., Ann Intern Med. 2010, Jan. 19, 152(2): 93-100, Narrative Review: The Role of Leptin in Human Physiology: Emerging Clinical Applications).

Patients who have no detectable leptin level in the case of lipodystrophy, hypothalamic amenorrhea and congenital leptin deficiency (CLD) are treated with leptin replacement therapy and administration of metreleptin. Metreleptin is a recombinant leptin analog which is made up of 147 amino acids of the mature human leptin plus a methionine residue at the N-terminus. It is a non-glycolyzed polypeptide with a disulfide bond between Cys-97 and Cys-147. The molecular weight is approximately 16.15 kDa.

Metreleptin is however not approved by the FDA (Food and Drug Administration, USA) for the treatment of patients with partial lipodystrophy, because there is no evidence that metreleptin is safe and effective in a heterogeneous group. Metreleptin therefore has very limited significance in the treatment of patients with conventional obesity as these patients have a high level of leptin and consequently exhibit central leptin resistance (Paz-Filho G. et al., Metabolism (2014), 1-11, Leptin treatment: Facts and expectations).

Mutations in the gene encoding leptin usually lead to the absence of circulating leptin and consequently to extreme obesity. Wabitsch et al. (N Engl J Med; 372; 1; Jan. 1, 2015; 48-54) found a homozygous mutation which leads to the change from guanine to thymine in position 298 in the case of a two-year-old boy with extreme obesity. In the translated leptin, this leads to an amino acid change from aspartic acid to tyrosine in sequence position 100 of the leptin (taking into account the signal peptide with the amino acids 1 to 21). The mutated protein is secreted, but does not bind to the leptin receptor and does not activate it either. During treatment of the patient with metreleptin, normalization of the eating behavior and weight loss occurred.

The leptin level in the blood can for example be determined by means of RIA (radioimmunoassay) or ELISA (enzyme-linked immunoassay) (Kratzsch et al., Horm Res 2002; 57: 127-132: A Rapid Quantitative Immunofunctional Assay for Measuring Human Leptin).

SUMMARY OF THE INVENTION

In some examples, provided herein is an in-vitro method for detecting mutated leptin, the method comprises the following steps: determining the binding of non-mutated leptin from serum or plasma to human leptin receptor which binds non-mutated leptin, but does not bind mutated leptin or binds it with a maximum of 50% of the binding value of non-mutated leptin, giving a first binding value, wherein the mutated leptin in the amino acid sequence comprises at least one of the following amino acid changes D100Y, N103K, L72S, R105W, G133V, S141C or L161G; and determining the binding of both mutated leptin and non-mutated leptin from serum or plasma to a polyclonal or monoclonal antibody, wherein the polyclonal or monoclonal antibody binds both mutated leptin and non-mutated leptin, giving a second binding value, wherein mutated leptin is present when the first binding value is smaller than the second binding value, and wherein the binding values are determined by means of enzyme-linked immunosorbent assay (ELISA), radio immunoassay (RIA), fluorescence immunoassay (FIA), luminescence immunossay (LIA).

Also provided herein is an in-vitro method comprising using a test system for detecting mutated leptin in an isolated sample of an individual, wherein the test system comprises: a human leptin receptor which binds non-mutated leptin with a first binding value, but does not bind mutated leptin or binds it with a maximum of 50% of the binding value of non-mutated leptin, in the in-vitro diagnosis of obesity, wherein the mutated leptin in the amino acid sequence has at least one of the following amino acid changes D100Y, N103K, L72S, R105W, G133V, S141C or L161G.

Also provided herein is a method of treating a patient suffering from obesity, comprising: a) providing a first sample isolated from the patient at a first time, b) determining binding of non-mutated leptin to a first detection reagent in said first sample and obtaining a first value, c) providing at least a second sample isolated from said patient at a second time, wherein said second time is later than said first time, d) determining binding of both mutated leptin and non-mutated leptin from the second sample to a second detection reagent and obtaining a second value, e) calculating a quotient Q, wherein quotient Q=(first binding value)/(second binding value), f) determining the genetic status of the patient based upon quotient Q, wherein a quotient Q of 0.1 or less is an indication that the patient is homozygous, or wherein a quotient Q between 0.8 and 0.1 is an indication that the patient is heterozygous, and g) developing a suitable treatment regimen based upon the patient's genetic status.

BRIEF DESCRIPTION OF THE DRAWINGS

The foregoing summary, as well as the detailed description, will be better understood when read in conjunction with the appended drawings. The present invention is described herein in greater detail using an embodiment and associated drawings. In the drawings:

FIG. 1a shows SEQ ID NO: 1. SEQ ID NO: 1 is the human leptin precursor sequence, which comprises the mature leptin (amino acids 22 to 167) as well as the N-terminal signal peptide (amino acids 1 to 21);

FIG. 1b shows SEQ ID NO: 2. SEQ ID NO: 2 is the human leptin precursor sequence of a mutated leptin, which contains a change from aspartic acid (D) to tyrosine (Y) at the amino acid position 100;

FIG. 1c shows SEQ ID NO: 3. SEQ ID NO: 3 is the human leptin precursor sequence of a mutated leptin, which contains a change from asparagine (N) to lysine (K) at the amino acid position 103;

FIG. 1d shows SEQ ID NO: 4. SEQ ID NO: 4 is the human leptin precursor sequence of a mutated leptin, which contains a change from leucine (L) to serine (S) at the amino acid position 72;

FIG. 2a shows SEQ ID NO: 5, which is the human leptin receptor sequence of isoform A;

FIG. 2b shows SEQ ID NO: 6, which is the human leptin receptor sequence of isoform B;

FIG. 2c shows SEQ ID NO: 7, which is the human leptin receptor sequence of isoform C;

FIG. 2d shows SEQ ID NO: 8, which is the human leptin receptor sequence of isoform D;

FIG. 2e shows SEQ ID NO: 9, which is the human leptin receptor sequence of isoform E; and FIG. 2f shows SEQ ID NO: 10, which is the fragment Thr20 to Asp839 of the human leptin receptor sequence of isoform B.

DETAILED DESCRIPTION

The object of the present invention is to provide a method which allows an improved differential diagnosis in the case of obesity. A further object of the invention is to provide means for carrying out such a method.

The object of the invention is achieved by provision of a compilation of detection reagents, wherein the compilation comprises a first and a second detection reagent, wherein the first detection reagent binds non-mutated leptin with a first binding value, but does not bind mutated leptin or binds it with a maximum of 50% of the binding value of non-mutated leptin, and wherein the second detection reagent binds both mutated and non-mutated leptin with a second binding value.

The object of the invention is furthermore achieved by a method for detecting mutated leptin in vitro, wherein the method comprises the following steps:

determining the binding of non-mutated leptin from a, preferably first, liquid sample material to a first detection reagent, giving a first binding value, determining the binding of both mutated leptin and non-mutated leptin from a, preferably second, liquid sample material to a second detection reagent, giving a second binding value, wherein mutated leptin is present when the first binding value is smaller than the second binding value.

The determination of the binding of non-mutated leptin from or in a, preferably first, liquid sample material and the determination of the binding of both mutated leptin and non-mutated leptin from or in a, preferably second, liquid sample material can be carried out independently of each other. For example, the determination of these two parameters can thus take place independently of each other in terms of time and space.

The preferably first and the preferably second liquid sample materials were isolated from the same subject before the method according to the invention was carried out.

The preferably first and the preferably second sample materials can, according to a variant of the invention, originate from one extraction from a subject, which was then divided into two, three, four or more sample materials. In these sample materials obtained in this way, according to a variant, the two parameters, i.e. the binding of non-mutated leptin on the one hand and the binding of both mutated leptin and non-mutated leptin on the other hand, can then be carried out separately from each other in terms of time and space or correlated with each other in terms of time and/or space.

The preferably first and the preferably second sample materials can, according to a further variant of the invention, also have been extracted from a subject separately from each other in terms of time and/or space. Consequently in this variant of the invention, the first and the second sample materials can originate from different extractions from a subject, for example a human.

According to a further variant of the invention, the preferably first and the preferably second sample materials can, before the determination of the respective binding, also have been further processed and/or prepared differently, preferably depending on the detection reagent used in each case.

Within the meaning of the invention, by a first or second detection reagent is meant in each case both a single detection reagent and a plurality of detection reagents, in particular one or more detection molecule(s). Thus, within the meaning of the Invention, a detection reagent, in particular, one detection molecule or several detection molecules, can be, for example, a combination of detection molecules such as for example a primary antibody and secondary antibody and/or further antibodies and/or leptin receptor molecule(s).

The secondary antibody and/or further antibodies, for example a tertiary antibody, can be detectably labeled, for example with a radioisotope, fluorophore, oligonucleotide, biotin or with detectable particles, for example gold particles.

The secondary antibody and/or further antibodies can also be coupled to an enzyme, for example a reporter enzyme, with the result that a binding is detected by enzymatic reaction. For example, the enzyme coupled to an antibody can be horseradish peroxidase, alkaline phosphatase, etc.

An antibody can be a monoclonal or polyclonal antibody. Instead of antibodies, antibody structures such as for example the antibody fragments or antibody elements specified below can also be used.

Within the meaning of the invention, by detection reagent, in particular detection molecule(s), is also meant further binding structures which facilitate a binding of non-mutated leptin, but no binding of mutated leptin or a binding thereof with a maximum of 50% of the binding value of non-mutated leptin, on the one hand or of mutated and non-mutated leptin on the other hand. According to a variant of the invention, by the term detection reagent is thus also meant a leptin receptor or a fragment of a leptin receptor which binds non-mutated leptin, but does not bind mutated leptin or binds it with a maximum of 50% of the binding value of non-mutated leptin. Instead of the leptin receptor, other specific receptor structures, for example aptamers, can also be used. The aptamers can be DNA or RNA oligonucleotides. Peptide aptamers can, however, also be used.

The term "detection reagent" encompasses within the meaning of the invention both a single detection reagent and several detection reagents, unless otherwise Indicated.

The object of the invention is also achieved by use of one detection reagent or several detection reagents which binds or bind non-mutated leptin with a first binding value, but does or do not bind mutated leptin or binds or bind it with a maximum of 50% of the binding value of non-mutated leptin, in the diagnosis, preferably differential diagnosis, in the case of obesity.

Within the meaning of the invention, by a "compilation of detection reagents" is meant any arrangement which comprises both the first and the second detection reagent.

This arrangement can be for example a preferably immunological test system. The immunological test system can be selected from an RIA (radioimmunoassay), ELISA (enzyme-linked immunoassay), FIA (fluorescence immunoassay) or LIA (luminescence immunoassay). The test system can, however, also be a Western blot, a chromatography, for example affinity chromatography, a cell assay, a particle-based assay, as well as in each case a multiplex assay of this type, or a biochip, each of which comprises both the first and the second detection reagent.

By the "first detection reagent" and "second detection reagent" are meant in particular affinity-based detection reagents. According to the invention, by "affinity-based detection reagents" are meant for example aptamers, e.g. DNA aptamers, RNA aptamers or peptide aptamers, monoclonal antibodies, polyclonal antibodies, antibody fragments, for example Fab, $F(ab)_2$, Fv or scFv antibody fragments.

According to a preferred development, by "affinity-based detection reagents" are meant in particular monoclonal antibodies, polyclonal antibodies, antibody fragments, for example Fab, $F(ab)_2$, Fv or scFv antibody fragments.

The monoclonal antibodies or antibody fragments can be produced by conventional methods, for example hybridoma technology or phage display technology, and selected by conventional screening methods with respect to their specificity.

In addition, both the first and the second detection reagent can be a leptin receptor. According to the invention, by a "leptin receptor" is meant any specifically leptin-binding structure, for example naturally occurring leptin receptor or leptin receptor fragments. The leptin receptor structure can also be synthetic or mutated naturally occurring leptin receptors or leptin receptor fragments.

It is essential according to the invention that the first detection reagent binds non-mutated leptin, but does not bind mutated leptin or only binds it with a maximum of 50% of the binding value of non-mutated leptin. The first detection reagent preferably binds mutated leptin with a maximum of 40%, a maximum of 30%, a maximum of 20%, a maximum of 10% or a maximum of 5% of the binding value of non-mutated leptin. The first detection reagent most preferably binds non-mutated leptin, but does not bind mutated leptin or only binds it with a maximum of 5% or a maximum of 2% of the binding value of non-mutated leptin. The first detection reagent preferably binds no mutated leptin.

According to a most preferred variant of the invention, the first detection reagent is a leptin receptor. Surprisingly, the human leptin receptor differentiates selectively between non-mutated leptin and mutated leptin. The human leptin receptor is eminently suitable in its various isoforms for the selective detection of non-mutated leptin in the presence of mutated leptin. Instead of the whole leptin receptor or the various whole Isoforms, the corresponding leptin receptor fragments and/or modified leptin receptors and/or modified leptin receptor fragments can also be used. For example, the leptin binding domain of the leptin receptor or a fusion protein which contains the leptin receptor binding domain can be used. The leptin receptors, in fragmented and/or modified form, are characterized by their function of the selective binding of non-mutated leptin. Instead of the human leptin receptor, other binding structures which selectively detect non-mutated leptin, in particular aptamers, can also be used.

According to the invention, by "binding value" is meant the measured value, characteristic of the measuring system used in each case, for the binding of detection reagent to non-mutated leptin on the one hand or non-mutated and mutated leptin on the other hand. This measured value can, either directly or indirectly, be a measure of the binding affinity.

The measured value reflecting the binding affinity represents a measure of the binding of the first detection reagent to non-mutated leptin. In the case of the second detection reagent, the measured value reflecting the binding affinity represents a measure of the binding of both mutated and non-mutated leptin.

The measured value representing the binding value can for example have the unit of a concentration (or of a quantity). For example in the case of RIA, ELISA, FIA or LIA, on the one hand the concentration (or quantity) of non-mutated leptin which is capable of binding or on the other hand the concentration (or quantity) of non-mutated and mutated leptin which is capable of binding is thus usually determined in one test sample.

The measured value representing the binding value can also be expressed as equilibrium constant $K_D$, i.e. as chemical equilibrium within the meaning of the law of mass action.

According to a variant of the invention, the binding affinity is correlated with the equilibrium constant $K_D$:

$$K_D=(C_N \cdot C_L)/C_{NL}.$$

wherein:
$C_N$ represents the concentration of the detection reagent,
$C_L$ represents the concentration of (non-mutated or non-mutated and mutated) leptin, and
$C_{NL}$ represents the concentration of the complex of detection reagent and (non-mutated or non-mutated and mutated) leptin.

The smaller the $K_D$ value, the greater the binding affinity.

Another suitable signal such as fluorescence, radioactivity measurement or the like can also be used as binding value.

In the invention, the binding value is preferably expressed as a concentration, with the result that concentrations are therefore compared with each other.

According to a variant of the invention, it is preferred that the binding value, i.e. the measured value determined in each case, for the binding of non-mutated leptin to the first detection reagent as well as of non-mutated leptin and mutated leptin to the second detection reagent is determined under in each case substantially identical, preferably under identical, measurement conditions.

The respective measurement can therefore be carried out under identical temperature conditions, for example 20° C. or 25° C., under substantially identical buffer conditions, for example with phosphate-buffered salt solution pH 7.5, with substantially identical dilutions for a substantially identical period, for example 2 hours.

However, it has surprisingly transpired that the detection of the binding or the determination of the binding value can also be carried out with a reliable result when the first binding value, i.e. the determined measured value, for the binding of non-mutated leptin to the first detection reagent, wherein mutated leptin is not bound or is bound with a maximum of 50% of the binding value of non-mutated leptin, and the second binding value of the binding of mutated as well as non-mutated leptin to the second detection reagent are determined under in each case substantially different, in particular under different, measurement conditions and/or using different measurement methods. The different measurement conditions can also be in particular different measurement methods. In the case of an identical measurement method, the conditions under which the measurements are carried out can in particular differ from each other.

Thus, for example, the binding value of mutated and non-mutated leptin, which therefore corresponds to a binding value of the total leptin ("total leptin"), can be determined using a conventional detection method, for example an affinity-based detection method, for example using an immunological test such as an ELISA, RIA, FIA, LIA, etc. In or from a preferably liquid sample material of a subject.

The binding value of non-mutated leptin is carried out using a detection method or using a compilation of detection reagents, for example a test system, in which the detection reagent or detection reagents differentiate(s) between mutated and non-mutated leptin, and therefore binds non-mutated leptin and does not bind mutated leptin or binds it with a maximum of 50% of the binding value of non-mutated leptin. A leptin receptor or variants of a leptin receptor are preferably used here. The preferably human leptin receptor surprisingly has an extraordinary specificity for non-mutated leptin, and therefore preferably does not or does not detectably bind mutated leptin.

Irrespective of any possible variations on the one hand in the determination of the binding value in the case of total leptin, i.e. of mutated and non-mutated leptin, and on the other hand in the determination of the binding value of non-mutated leptin, wherein mutated leptin does not bind or binds with a maximum of 50% of the binding value of non-mutated leptin, the respective binding values are surprisingly significantly different, with the result that a differential diagnosis can be carried out.

Thus, for example, the compilation according to the invention or the method according to the invention can be used to ascertain whether heterozygosity or homozygosity with respect to mutated leptin is present in a subject, preferably a human.

The method according to the invention for detecting mutated leptin is carried out in vitro using isolated sample material. The method according to the Invention is therefore not carried out in vivo.

According to a preferred development of the invention, the first detection reagent Is a polyclonal antibody, monoclonal antibody or a leptin receptor which binds non-mutated leptin, but does not bind mutated leptin or binds it with a maximum of 50% of the binding value of non-mutated leptin.

According to a further preferred embodiment of the invention, the second detection reagent is a polyclonal or monoclonal antibody, wherein the polyclonal or monoclonal antibody binds both mutated and non-mutated leptin.

According to a preferred variant, the second detection reagent is a polyclonal antibody which binds both mutated leptin and non-mutated leptin.

Polyclonal antibodies can be produced in the conventional manner. For example, polyclonal antibodies against human leptin can be produced by immunizing animals with leptin, optionally with adjuvants. Animals which can be used are for example goats, rabbits, mice or rats. The antibodies produced by the different B cells recognize a plurality of epitopes on the leptin, with the result that both mutated and non-mutated leptin are recognized by the polyclonal antibodies.

Alternatively, monoclonal antibodies can also be used.

The B cells obtained after immunization with leptin are fused with a myeloma cell in the conventional manner (hybridoma technology).

The hybridomas obtained are then separated and selected with respect to the antibodies produced by the hybridoma cells with regard to the specificity thereof. In this way, monoclonal antibodies which recognize both mutated and non-mutated leptin can be isolated. The production of monoclonal antibodies and the selection of hybridoma cells for the specificity of the antibodies are known to a person skilled in the art.

According to a most preferred embodiment, the first detection reagent is a leptin receptor, preferably a human leptin receptor. According to a further variant of the invention, the first detection reagent is a leptin receptor fragment, a modified leptin receptor and/or a modified leptin receptor fragment. For example, the first detection reagent can be the leptin binding domain of the leptin receptor or a fusion protein which contains the leptin binding domain of the leptin receptor. The above-named leptin receptor fragments and/or modifications have the function of selection between mutated and non-mutated leptin.

According to a further preferred embodiment of the invention, the leptin receptor comprises the leptin binding domain of the human leptin receptor, preferably of isoform A, isoform B, isoform C, isoform D and/or isoform E.

The leptin receptor is a membrane-bound receptor which has an extracellular leptin binding domain. The extracellular leptin binding domain is connected to a cytoplasmic domain via a transmembrane region.

In humans, there are five isoforms, isoform A, isoform B, isoform C, isoform D and isoform E, which represent alternative splice variants.

Isoform B is the longest variant of the leptin receptor.

Isoform A, isoform C and isoform D of the human leptin receptor differ with respect to the cytoplasmic domains. The cytoplasmic domains are connected to the Janus kinase (JAK). During binding of leptin to the leptin receptor, the aggregation of receptor homodimers occurs, causing an activation of the Janus kinase. In the course of the activation, the phosphorylation of cytoplasmic transcription factors STATs, in particular STAT-3, occurs. The activated signal transducers and activators of transcription (STATs) migrate to the cell nucleus and bring about gene transcription.

Isoforms A, C and D make only an insignificant contribution to the signal transcription.

Isoform E is a soluble form of a leptin receptor, which is probably cleaved off from the cell surface by proteolytic cleavage in the context of a receptor shedding.

According to the invention, the leptin binding domain or isoform E of the leptin receptor is, according to a preferred embodiment, used as first detection reagent.

The leptin binding domain can also be used as fusion proteins. According to a variant according to the Invention, the leptin binding domain or isoform E can thus be fused with the Fc part of an antibody. During fusion with the Fc part of an antibody, homodimers of the leptin binding domain can be provided. These homodimers are similar to the homodimers induced in vivo during natural leptin binding on a cell.

According to a preferred variant of the invention, the amino acids Thr20 to Asp839 of isoform B are used in the production of a fusion protein. The amino acids Thr20 to Asp839 of isoform B are preferably fused with the Fc part of an antibody, preferably as homodimer. Alternatively, for example, isoform E is also suitable according to the invention in the production of fusion proteins, for example with the Fc part of an antibody, optionally as homodimer.

It has surprisingly been shown that the leptin binding domain of the natural leptin receptor selectively binds non-mutated leptin.

Leptin receptors the sequence of which is not identical to that of the natural leptin receptor can also be used as first detection reagent.

According to the Invention, it is therefore possible to use leptin receptor variants of the natural leptin receptor in which amino acids are deleted or substituted by other amino acids, provided that non-mutated leptin is still specifically bound.

According to a preferred development, the leptin receptor used has at least a sequence identity of 80%, preferably of at least 90%, further preferably of at least 95%, even further preferably of at least 98%, preferably of at least 99%, relative to the sequence of the natural leptin receptor.

According to a further preferred development of the invention, the leptin receptor is a soluble isoform which preferably contains the amino acids Thr20 to Asp839 of Isoform B of the human leptin receptor.

According to a preferred development, the leptin receptor used has at least a sequence identity of 80%, preferably of at least 90%, further preferably of at least 95%, even further preferably of at least 98%, even further preferably of at least 99%, relative to the sequence of the soluble isoform of the natural leptin receptor, which preferably contains the amino acids Thr20 to Asp839 of isoform B.

According to a further preferred embodiment of the invention, the mutated leptin in the amino acid sequence has at least one of the following amino acid changes D100Y, N103K and/or L72S. The sequence data in the present invention relate to the leptin sequence including signal peptide, unless otherwise indicated.

According to a further preferred embodiment of the invention, the mutated leptin in the amino acid sequence has at least one of the following amino acid changes R105W, G133V, S141C and/or L161G.

According to a further preferred embodiment of the Invention, the mutated leptin in the amino acid sequence has at least one of the following amino acid changes D100Y, N103K, L72S, R105W, G133V, S141C and/or L161G.

According to a further preferred embodiment of the invention, the mutated leptin in the amino acid sequence has at least one amino acid change D100Y.

In a preferred embodiment, the mutated leptin in the amino acid sequence has the amino add change D100Y.

In a preferred embodiment, the mutated leptin in the amino acid sequence has the amino acid change N103K.

In a preferred embodiment, the mutated leptin in the amino acid sequence has the amino acid change L72S.

In a preferred embodiment, the mutated leptin in the amino acid sequence has the amino acid change R105W.

In a preferred embodiment, the mutated leptin in the amino acid sequence has the amino acid change G133V.

In a preferred embodiment, the mutated leptin in the amino acid sequence has the amino acid change S141C.

In a preferred embodiment, the mutated leptin in the amino acid sequence has the amino acid change L161G.

It has surprisingly been shown that the natural leptin receptor highly selectively binds non-mutated leptin or does not significantly bind, preferably does not bind, mutated leptin.

Thus, in the case of an amino acid change in the leptin, for example at the sequence position 100 from D to Y (D100Y), the mutated leptin is already no longer bound by the natural binding domain of the leptin receptor. In a most preferred variant of the invention, the mutated leptin has an amino acid change from D to Y at the sequence position 100.

The method according to the invention for detecting mutated leptin comprises the following steps:

- determining the binding of non-mutated leptin from a, preferably first, liquid sample material to a first detection reagent, giving a first binding value, determining the binding of both mutated leptin and non-mutated leptin from a, preferably second, liquid sample material to a second detection reagent, giving a second binding value, wherein mutated leptin is present when the first binding value is smaller than the second binding value.

According to a variant of the invention, the preferably first and the preferably second liquid sample materials were isolated from the same subject together, before the method according to the invention was carried out. According to a further variant of the invention, the extraction of the sample material from a subject took place at different points in time.

Depending on the measurement method used, the determination of the first binding value and the second binding value can be carried out in one identical test sample or separately in two test samples. In the first case the binding values are determined together in one test sample and in the second case the sample material is divided into two test samples and measured separately, but optionally in parallel. According to a further variant of the invention, the determination of the first binding value and the second binding value takes place at different points in time and optionally under different measurement conditions and/or optionally using different measurement methods.

The subject is preferably a mammal, further preferably a human.

The, preferably first and preferably second, liquid sample material can be for example the serum or plasma from a blood sample extracted from a subject, preferably a human. After the blood has been taken, the cellular portion of the blood can be separated off before coagulation or after coagulation. If the separation takes place before coagulation, blood plasma is obtained; if the separation takes place after coagulation, blood serum is obtained.

According to the invention, both blood plasma and blood serum can be used as, preferably first and preferably second, liquid sample material.

According to a preferred variant of the invention, blood serum is used.

After separation of the cellular components, the blood sample can be separated in order to obtain a preferably first and a preferably second liquid sample material.

After suitable dilution, for example in a buffer, for example in phosphate-buffered saline, tris-buffered saline or sodium bicarbonate buffer, the thus-diluted, preferably first and preferably second, liquid sample material is brought into contact with the first or the second detection reagent respectively and then the respective binding value is determined.

The measured value representing the binding value can be determined by various methods, wherein, for example after setting equilibrium conditions, the concentration of free detection reagent, free leptin and/or the concentration of the complex comprising detection reagent and leptin can be determined.

For example, a binding value can be determined by means of equilibrium dialysis, ultrafiltration, chromatography, electrophoresis, centrifugation or biomolecular interaction analysis (BIA).

The binding value, which represents a measure of the affinity, can also be determined via a competition assay. The competition assay can be carried out for example in the form of an RIA, ELISA, FIA or LIA in the conventional manner.

According to a variant of the method according to the invention, in the determination of the binding value as a measure of the affinity, an identical measurement method under identical conditions can in each case be carried out both in the case of the determination of the first binding value and in the case of the determination of the second binding value.

According to a further development of the method according to the invention, the determination of the first binding value and the second binding value takes place in a single test sample.

In this development of the invention, separation into a first and a second liquid sample material is not necessary. Rather, the determination of the first binding value using the first detection reagent and the determination of the second binding value using the second detection reagent take place in one test sample, for example in one measurement volume. The measurement of the two binding values preferably takes place simultaneously or virtually simultaneously.

Suitable measurement methods are those in which the first and the second detection reagents are coupled to particulate solid phases. These particulate solid phases, to which in each case the first or second detection reagent is coupled, can for example be distinguished by means of different fluorescence properties, for example as a result of the use of different fluorescent dyes, and can be measured together, preferably simultaneously, for example by means of flow cytometry. These particle-based assays are known to a person skilled in the art, for example, as "bead-based multiplex assays". Measurement using particle-based multiplex methods can also be carried out using biochips.

According to a most preferred variant, the determination of the first binding value and the second binding value takes place at different points in time and optionally under different measurement conditions and/or optionally using different measurement methods, as stated above.

If the first binding value is lower than the second binding value, then this is evidence that the sample material contains mutated leptin. The proportion of mutated leptin is then a measure of the proportion of physiologically inactive leptin.

When the first detection reagent is used the binding of non-mutated leptin is measured. In the determination of the second binding value the binding of both mutated leptin and non-mutated leptin is measured using the second detection reagent. The binding value of mutated and non-mutated leptin can also be referred to as the binding value of the total leptin, therefore "total leptin".

If the, preferably first and preferably second, liquid sample material obtained from the same subject contains no mutated leptin, then the first binding value contained with the first detection reagent is identical or virtually identical to the second binding value obtained using the second detection reagent. By "virtually identical" Is meant that the first and the second binding values differ by preferably up to less than 20%, further preferably by up to less than 15%.

According to the invention, the method used is preferably an ELISA, RIA, FIA or LIA, most preferably an ELISA.

According to a variant of the method according to the invention, the determination of the first binding value and the second binding value takes place in different test samples, preferably at different points in time and optionally using different determination methods.

According to a further variant of the method according to the invention, the determination of the first binding value and the second binding value takes place using different determination methods.

According to a further variant of the method according to the invention, a quotient Q formed from the first and the second binding value:

$$Q=\text{(first binding value)/(second binding value)}$$

is between 0.8 and 1.2, preferably between 0.9 and 1.1, or between 0.3 and 0.7, preferably between 0.4 and 0.6, or less than 0.2, preferably less than 0.1.

According to a further variant of the method according to the invention, the first and/or second detection reagent in each case comprises a combination of two or more detection reagents, in particular of detection molecules.

The method according to the invention is preferably suitable for the in-vitro diagnosis of obesity, wherein a quotient Q formed from the first and the second binding value:

Q=(first binding value)/(second binding value)

between 0.8 and 1.2, preferably between 0.9 and 1.1, indicates homozygosity in the obesity gene with respect to non-mutated leptin;
between 0.3 and 0.7, preferably between 0.4 and 0.6, indicates heterozygosity in the obesity gene with respect to mutated and non-mutated leptin; and
less than 0.2, preferably less than 0.1, indicates homozygosity with respect to mutated leptin.

According to a further preferred variant of the invention, a quotient Q formed from the first and second binding value:

Q=(first binding value/second binding value) is 0.8 or less.

Further preferably the quotient Q is 0.7 or less, 0.6 or less, 0.5 or less, 0.4 or less, 0.3 or less, 0.2 or less or 0.1 or less.

A value of 0.1 or less or a value heading towards 0 is an indication that the patient is homozygous with respect to a leptin mutation or mutated leptin respectively. If the quotient is between 0.8 and 0.1, further preferably between 0.6 and 0.3, then this is an indication that the patient is heterozygous with respect to the leptin mutation. In this case, the patient secretes both non-mutated and mutated leptin.

The outcome of the method according to the invention enables a differential diagnosis in the case of obesity.

If a considerable proportion of mutated leptin is present, this is of great importance for the physician in the context of a differential diagnosis. In this case, although the patient may have a greatly increased level of leptin, wherein this leptin comprises both mutated and non-mutated leptin, the administration of a leptin substitute, for example metreleptin, can be indicated in order to treat the obesity and possibly further physiological disorders.

If a subject, preferably a mammal, for example a human, is heterozygous with respect to mutated and non-mutated leptin and therefore carries both the allele for non-mutated leptin and the allele for mutated leptin, this may not be recognized during determination of the total leptin. However, the present invention facilitates a differential diagnosis which allows treatment, in particular, of heterozygous subjects, for example with metreleptin.

The present invention also allows a quick in-vitro diagnosis of a genetic disease at the protein level with respect to mutated leptin. Therefore when both father and mother are heterozygous with respect to mutated leptin, there can be clarification regarding the potential risks of obesity in any offspring. Within the framework of a prenatal diagnosis, it can therefore be ascertained or confirmed specifically whether or that there is a risk of genetic obesity.

The present invention therefore allows a differential diagnosis which facilitates a novel treatment approach in the case of patients who only or also synthesize mutated leptin.

Depending on the quotient Q formed from the first binding value and second binding value, a diagnosis can furthermore be made with regard to the estimated quantity of leptin substitute, for example metreleptin, to be administered.

For patients affected by obesity, in particular children and young people, the present invention represents a significant advancement in the diagnosis, in particular differential diagnosis, and treatment in the case of obesity.

According to a further preferred embodiment of the method according to the invention, a polyclonal antibody, monoclonal antibody or a leptin receptor which binds non-mutated leptin, but does not bind mutated leptin or binds it with a maximum of 50% of the binding value of non-mutated leptin, is used as the first detection reagent.

According to a further preferred embodiment of the method according to the invention, a polyclonal or monoclonal antibody, wherein the polyclonal or monoclonal antibody binds both mutated leptin and non-mutated leptin, is used as the second detection reagent.

According to a most preferred embodiment of the method according to the invention, a leptin receptor, preferably a human leptin receptor, is used as first detection reagent. According to a further variant of the invention, a leptin receptor fragment, a modified leptin receptor and/or a modified leptin receptor fragment is used as first detection reagent. For example, the first detection reagent can be the leptin binding domain of the leptin receptor or a fusion protein which contains the leptin binding domain of the leptin receptor. The above-named leptin receptor fragments and/or modifications have the function of selection between mutated and non-mutated leptin.

According to a further preferred embodiment of the method according to the invention, it is preferred for the leptin receptor to comprise the leptin binding domain of the human leptin receptor, preferably of isoform A, isoform B or isoform D.

According to a further preferred development of the method according to the invention, the leptin receptor is a soluble isoform and preferably contains the amino acids Thr20 to Asp839.

It is furthermore preferred for the mutated leptin in the amino acid sequence to have at least one of the following amino acid changes at the sequence positions D100Y, N103K and/or L72S. The sequence data relate to the leptin sequence including signal peptide.

According to a further preferred embodiment of the invention, the mutated leptin in the amino acid sequence has at least one of the following amino acid changes R105W, G133V, S141C and/or L161G.

According to a further preferred embodiment of the invention, the mutated leptin in the amino acid sequence has at least one of the following amino acid changes D100Y, N103K, L72S, R105W, G133V, S141C and/or L161G.

According to a further preferred embodiment of the invention, the mutated leptin in the amino acid sequence has at least one amino acid change D100Y.

The method is preferably an immunological method, further preferably an ELISA, RIA, FIA or LIA.

The statements made above with respect to the compilation of detection reagents according to the invention apply correspondingly to the method according to the Invention.

The present invention furthermore relates to the use of a detection reagent which binds non-mutated leptin with a first binding value, but does not bind mutated leptin or binds it with a maximum of 50% of the binding value of non-mutated leptin, in the diagnosis of obesity.

The detection reagent is preferably used in the differential diagnosis of obesity.

The detection reagent is preferably a polyclonal antibody, monoclonal antibody or a leptin receptor.

According to a further preferred embodiment of the use according to the invention, the detection reagent, referred to below as first detection reagent, is used together with a second detection reagent. The second detection reagent binds both mutated and non-mutated leptin with a second binding value.

According to a preferred development of the use according to the invention, the second detection reagent Is a polyclonal or monoclonal antibody, wherein the polyclonal or monoclonal antibody binds both mutated leptin and non-mutated leptin.

According to the invention, it is furthermore preferred for the leptin receptor used as first detection reagent to comprise the leptin binding domain of the human leptin receptor, preferably of isoform A, isoform B or isoform D.

According to a further development of the use according to the invention, the leptin receptor used as first detection reagent is a soluble isoform and preferably contains the amino acids Thr20 to Asp839 of isoform B.

It is furthermore preferred for the mutated leptin in the amino acid sequence to have at least one of the following amino acid changes at the sequence positions D100Y, N103K and/or L72S, wherein the sequence numbering refers to the amino acid sequence including signal peptides.

According to a preferred development of the use according to the invention, the mutated leptin has an amino acid change D100Y in the sequence of the natural leptin.

According to a preferred development of the use according to the invention, the mutated leptin has an amino acid change N103K in the sequence of the natural leptin.

According to a preferred development of the use according to the invention, the mutated leptin has an amino acid change L72S in the sequence of the natural leptin.

The method is preferably an immunological method, further preferably an ELISA, RIA, FIA or LIA.

The statements made regarding the compilation of detection reagents according to the invention or regarding the method according to the invention apply correspondingly to the use according to the invention.

The present invention relates, according to a preferred embodiment, to the use of a detection reagent which binds non-mutated leptin with a first binding value, but does not bind mutated leptin or binds it with a maximum of 50% of the binding value of non-mutated leptin, in the diagnosis of obesity.

The present invention relates, according to a further preferred embodiment, to the use according to the invention in the in-vitro determination of homozygosity or heterozygosity with respect to the obesity gene, which encodes mutated leptin and/or non-mutated leptin, of a mammal, preferably a human.

The use according to the invention therefore surprisingly allows, in particular in isolated sample materials, an extremely reliable differential diagnosis in the case of obesity, in particular with respect to homozygosity and heterozygosity in the obesity gene, which encodes leptin and mutated leptin respectively, at the protein level, in particular using an immunological test system or immunological test method. Immunological test methods can be designed as rapid tests. In particular, the use according to the invention allows mass screenings to be carried out simply. If desired, for confirmation, laborious genetic analyses can then be carried out subsequently for the conspicuous samples.

The following figures and examples serve to illustrate the invention, but without limiting the invention.

Figures

FIG. 1a shows the human leptin precursor sequence, which comprises the mature leptin (amino acids 22 to 187) as well as the N-terminal signal peptide (amino acids 1 to 21).

FIG. 1b shows the human leptin precursor sequence of a mutated leptin, which contains a change from aspartic acid (D) to tyrosine (Y) at the amino acid position 100.

FIG. 1c shows the human leptin precursor sequence of a mutated leptin, which contains a change from asparagine (N) to lysine (K) at the amino acid position 103.

FIG. 1d shows the human leptin precursor sequence of a mutated leptin, which contains a change from leucine (L) to serine (S) at the amino acid position 72.

FIG. 2a shows the human leptin receptor sequence of isoform A.

FIG. 2b shows the human leptin receptor sequence of isoform B.

FIG. 2c shows the human leptin receptor sequence of isoform C.

FIG. 2d shows the human leptin receptor sequence of isoform D.

FIG. 2e shows the human leptin receptor sequence of isoform E.

FIG. 2f shows the fragment Thr20 to Asp839 of the human leptin receptor sequence of isoform B.

EXAMPLES

Example 1a

In-vitro Detection of Total Leptin

Polystyrene microtiter plates customary in the trade (Greiner Bio-One GmbH, Frickenhausen, DE—C8 type, Flat Bottom, No. 705071) were used for the production of a total leptin ELISA.

A commercially available monoclonal mouse anti-human leptin IgG1 primary antibody in a concentration of 2 µg/ml in phosphate-buffered saline (PBS) at pH 7.4 was adsorptively bound to these polystyrene microtiter plates as solid phase.

For this, the plates were incubated, cooled (2° C. to 8° C.), overnight in a wet chamber. The antibody solution was then extracted by suction, and unsaturated binding sites on the polystyrene surface were saturated with bovine serum albumin (BSA) in a 1% solution in PBS over 4 hours at pH 7.4. The solution was extracted by suction and the plates were used directly or stored, dried, until use.

The measurements were carried out in duplicate. All incubations were carried out at room temperature (20° C. to 25° C.).

1. 100 µl dilution buffer (50 mM PBS buffer pH 7.4 with 0.5% BSA and 0.05% Tween-20 detergent) was placed in all required wells of the microtiter plates.
2. 20 µl dilution buffer was pipetted into the first 2 wells (blank value). Following this, in each case 20 µl leptin-standard or 20 µl of the sample to be measured was added.
3. The wells of the plate were covered with adhesive film and shaken at 200 to 350 rpm for 1 hour.
4. At the end of the incubation time, the solutions were extracted by suction and the plate was washed five times with 300 µl wash buffer WB (50 mM PBS buffer pH 7.4 with 0.5% BSA)/well. The wash buffer remained in the wells for approximately 15 seconds before the extraction by suction.

5. Following the last washing step, 100 µl of a horseradish peroxidase (POD) conjugate of an anti-mouse IgG1 antibody was pipetted into each well and the batch was shaken at 200 to 350 rpm for 30 minutes.
6. After completion of this incubation, the plate was washed 5×, as described in step 4).
7. 100 µl of the substrate solution, stabilized $H_2O_2$—tetramethylbenzidne, was pipetted into each well.
8. The plate was incubated in the dark for 15 minutes as the substrate is light-sensitive.
9. At the end of the Incubation time, 100 µl 0.1 M sulfuric acid was pipetted into each well.
10. The measurement of the color reaction took place within 30 minutes in a photometer for microtiter plates ("ELISA Reader") at 450 nm (reference filter ≥590 nm).

Samples which achieved higher absorbances than the standard with the highest concentration lay outside the standard curve. For reliable determination, these samples were measured again in a second performance of the test at higher dilution.

As ELISA standards, recombinant leptin (Mediagnost, Reutlingen, DE) was used in concentrations of 1, 10, 25, 50 and 100 ng/ml.

The average blank value OD was subtracted from the average values of the optical density (OD) of the standard concentrations and of the samples.

The standard concentrations (x-axis) were plotted against the measured optical density (y-axis) and a standard curve was generated.

The leptin concentration of the controls and of the samples respectively is obtained from the standard curve.

Example 1b

In-vitro Detection of Functional Leptin

For the detection of functional leptin, the test setup was varied such that a leptin receptor which binds non-mutated leptin, but does not bind mutated leptin or binds it with a maximum of 50% of the binding value of non-mutated leptin, was bound to polystyrene microtiter plates as solid phase.

A commercially available recombinantly produced molecule with the amino acid sequence Thr20-Asp839 of the human leptin receptor (Recombinant Human Leptin R Fc Chimera, Catalog Number 389-LR/CF, R & D Systems, Minneapolis, Minn., USA) was used as leptin receptor.

The leptin receptor was adsorptively bound to polystyrene microtiter plates in a concentration of 1.5 µg/ml in 10 mM sodium carbonate buffer at pH 9.6 overnight in a wet chamber in a cooled environment (2° C. to 8° C.).

The coating solution was then extracted by suction, and unsaturated binding sites on the polystyrene surface were saturated with bovine serum albumin in a 1% solution in PBS over 4 hours at pH 7.4.

The solution was extracted by suction and the plates were used directly or stored dried until use. The measurements were carried out in duplicate. All Incubations were carried out at room temperature (25° C.).

The samples or controls to be measured were diluted with dilution buffer (50 mM PBS buffer pH 7.4 with 0.5% BSA and 0.05% Tween-20 detergent) in a ratio of 1:10.
1. 100 µl standard and 100 µl pre-diluted control or sample solution respectively were pipetted into all required wells of the microtiter plates.
2. The wells of the plate were covered with adhesive film and shaken at 350 rpm for 2 hours.
3. At the end of the incubation time, the solutions were extracted by suction and the plate was washed three times with 300 µl wash buffer WB/well. The wash buffer remained in the wells for approximately 15 seconds before the extraction by suction.
4. Following the last washing step, 100 µl of a biotin conjugate of a commercially available polyclonal rabbit anti-human leptin antibody was pipetted into each well and the batch was shaken at 350 rpm for 30 minutes.
5. After completion of this Incubation, the plate was washed three times, as described in step 3.
6. Following the last washing step, e.g. 100 µl of a streptavin horseradish peroxidase conjugate Is pipetted into each well and the batch is shaken at 350 rpm for 30 minutes. After completion of this incubation, the plate was washed 3×, as described in step 3).
7. 100 µl of the substrate solution, stabilized $H_2O_2$—tetramethylbenzidine, was pipetted into each well.
8. The plate was incubated in the dark at 20° C. to 25° C. for 15 minutes as the substrate is light-sensitive.
9. At the end of the incubation time, 100 µl 0.1M sulfuric acid was pipetted into each well.
10. The measurement of the color reaction took place within 30 minutes in a photometer for microtiter plates ("ELISA Reader") at 450 nm (reference filter ≥590 nm).

Samples which achieved higher absorbances than the standard with the highest concentration lay outside the standard curve. For reliable determination, these samples were measured again in a second performance of the test at higher dilution.

As ELISA standards, recombinant leptin (Mediagnost, Reutlingen. DE) was used in concentrations of 0, 0.2, 1, 2.5, 5, 7.5 and 10 ng/ml.

The average blank value OD was subtracted from the average values of the optical density (OD) of the standard concentrations and of the samples.

The standard concentrations (x-axis) were plotted against the measured optical density (y-axis) and a standard curve was generated.

The leptin concentration of the diluted controls and of the samples respectively is obtained from the standard curve and, after multiplication by the dilution factor, the leptin concentration of the undiluted controls and samples respectively is then obtained.

Non-mutated functional leptin was measured in this test in a concentration which corresponds to the concentration measured for total leptin in the leptin ELISA.

Example 1c

Evaluation

Human leptin cDNA (NCBI Reference Sequence: NM_000230.2) was used to generate point mutations by site-directed mutagenesis.

For this, the Q5® Site-Directed Mutagenesis Kit from New England Biolabs GmbH (Frankfurt am Main, DE) was used, according to the manufacturer's specifications.

HEK293 cells were transiently transfected with human leptin (pcDNA3.1+-leptin_wt) or mutated leptin (pcDNA3.1+-leptin_D100Y or pcDNA3.1+-leptin_N103K), as described in Sambrook et al. (Molecular cloning: a laboratory handbook, $2^{nd}$ edition, 1998, Cold Spring Harbor Laboratory Press, Cold Spring Harbor, USA).

48 h after the transfection, the respective cells were lysed and 100 µl of the supernatants were used as samples 1 to 3 in the ELISA tests described in Example 1a and Example 1b.

Serum samples from 5 blood donors and purified recombinant human leptin and purified recombinant human leptin mutation D100Y were also used.

Measurement results from various samples using the tests described in Example 1a and Example 1b are shown in Table 1:

TABLE 1

Comparison of measured values of total against functional leptin

| Sample no.: | | Measured values functional leptin | Measured values total leptin |
|---|---|---|---|
| | HEK293 transiently expressed cell culture supernatants | | |
| 1 | Leptin non-mutated | 490.2 ng/ml | 577.7 ng/ml |
| 2 | Leptin mutation D100Y | <0.5 ng/ml | 193.1 ng/ml |
| 3 | Leptin mutation N103K recombinant leptin, purified | <0.35 ng/ml | 37.1 ng/ml |
| 4 | Leptin non-mutated | 277.7 µg/ml | 335.2 µg/ml |
| 5 | Leptin mutation D100Y International WHO standard for human leptin WHO IS NIBSC 97/594 | 108 ng/ml | 8.03 µg/ml |
| 6 | nominal 2 ng/ml: | 1.83 ng/ml | 1.84 ng/ml |
| 7 | nominal 6 ng/ml: Serum/plasma samples blood donor | 6.05 ng/ml | 6.1 ng/ml |
| 8 | CS-2 | 2.81 ng/ml | 2.46 ng/ml |
| 9 | DO-2226 | 4.61 ng/ml | 5.05 ng/ml |
| 10 | IDB-883- | 7.25 ng/ml | 8.31 ng/ml |
| 11 | IDB-8960 | 23.96 ng/ml | 25.05 ng/ml |
| 12 | BB-3935 | 34.12 ng/ml | 34.84 ng/ml |

It can be seen from Table 1 that a distinction can be made between mutated leptin and non-mutated leptin with the compilation according to the invention or the method according to the invention.

Sample no. 1 contains exclusively non-mutated leptin. The quotient of the concentration of non-mutated leptin (functional leptin) and total leptin is approximately 0.85 (490.2/577.7).

Sample no. 2 contains exclusively mutated leptin with the mutation D100Y. The quotient of the concentration of non-mutated leptin (functional leptin) and total leptin is <0.01 (0.5/193.1).

Sample no. 3 contains exclusively mutated leptin with the mutation N103K. The quotient of the concentration of non-mutated leptin (functional leptin) and total leptin is <0.01 (0.35/37.1).

Sample nos. 4 and 5 contain human leptin in a concentration of 2 ng/ml and 6 ng/ml respectively in accordance with the WHO standard. The quotient of the concentration of non-mutated leptin (functional leptin) and total leptin is 0.99 (1.83/1.84) and 0.99 (6.05/6.1) respectively.

Sample nos. 8 to 12 are serum/plasma samples from healthy blood donors. The quotient of the concentration of non-mutated leptin (functional leptin) and total leptin is 1.14 (2.81/2.46), 0.91 (4.61/5.05), 0.87 (7.25/8.31), 0.96 (23.96/25.05) and 0.98 (34.12/34.84) respectively.

Example 2

In the case of an obese infant (not shown in Table 1), a total leptin concentration of 30.1 ng/ml and a concentration of non-mutated leptin (functional leptin) of 0.3 ng/ml were determined in serum/plasma samples. The quotient of the concentration of non-mutated leptin (functional leptin) and total leptin is therefore 0.01 (0.3/30.1).

In the case of the father and mother, the concentration of non-mutated leptin (functional leptin) and total leptin respectively were then determined in the blood plasma/serum:

In the case of the father, a total leptin concentration of 2.3 ng/ml and a concentration of non-mutated leptin (functional leptin) of 1.2 ng/ml were determined in serum/plasma samples. The quotient of the concentration of non-mutated leptin (functional leptin) and total leptin is therefore 0.52 (1.2/2.3).

In the case of the mother, a total leptin concentration of 11.4 ng/ml and a concentration of non-mutated leptin (functional leptin) of 4.8 ng/ml were determined in serum/plasma samples. The quotient of the concentration of non-mutated leptin (functional leptin) and total leptin is therefore 0.42 (4.8/11.4).

From the measured concentration values of non-mutated leptin and total leptin and, respectively, the quotients calculated therefrom, it is immediately apparent that the father and mother are heterozygous with respect to mutated leptin and non-mutated leptin respectively.

The child of the father and mother is, however, homozygous with respect to mutated leptin.

The mutated leptin from father, mother and child was leptin with a D100Y mutation.

The compilation according to the invention and/or the method according to the invention therefore surprisingly allow an extremely reliable differential diagnosis in the case of obesity, in particular with respect to homozygosity and heterozygosity in the obesity gene which encodes leptin and mutated leptin respectively, at the protein level, in particular using an immunological test system or immunological test method. Immunological test methods can be designed as rapid tests. In particular, the method according to the invention is substantially quicker to carry out than genetic analyses, even within the framework of mass screenings.

The invention claimed is:

1. An in-vitro method for detecting mutated leptin, the method comprises the following steps:
   - determining the binding of non-mutated leptin from serum or plasma to human leptin receptor which binds non-mutated leptin, but does not bind mutated leptin or binds it with a maximum of 50% of the binding value of non-mutated leptin, giving a first binding value, wherein the mutated leptin in the amino acid sequence comprises at least one of the following amino acid changes D100Y, N103K, L72S, R105W, G133V, S141C and/or L161G, preferably D100Y, N103K and/or L72S, further preferably D100Y; and
   - determining the binding of both mutated leptin and non-mutated leptin from serum or plasma to a polyclonal or monoclonal antibody, wherein the polyclonal or monoclonal antibody binds both mutated leptin and non-mutated leptin, giving a second binding value,
   - wherein mutated leptin is present when the first binding value is smaller than the second binding value,
   - and wherein the binding values are determined by means of enzyme-linked immunosorbent assay (ELISA), radio immunoassay (RIA), fluorescence immunoassay (FIA), and luminescence immunossay (LIA).

2. The method according to claim 1, wherein the human leptin receptor comprises at least one of isoform A, isoform B, isoform C, isoform D, or isoform E.

3. The method according to claim 1, wherein the leptin receptor is a soluble isoform.

4. The method according to claim 1, wherein the determination of the first binding value and the second binding value takes place in one test sample.

5. The method according to claim 1, wherein the determination of the first binding value and the second binding value takes place in different test samples and at different points in time.

6. The method according to claim 1, wherein the determination of the first binding value and the second binding value takes place using different determination methods.

7. The method according to claim 1, wherein a quotient Q formed from the first and the second binding value:

$Q$=(first binding value)/(second binding value)

is between 0.8 and 1.2.

8. The method according to claim 1, wherein a quotient Q formed from the first and the second binding value:

$Q$=(first binding value)/(second binding value)

is 0.8 or less.

9. The method according to claim 1, wherein, for the in-vitro diagnosis of obesity, a quotient Q formed from the first and the second binding value:

$Q$=(first binding value)/(second binding value)

between 0.8 and 1.2 indicates homozygosity in the obesity gene with respect to non-mutated leptin;

between 0.3 and 0.7 indicates heterozygosity in the obesity gene with respect to mutated and non-mutated leptin; and less than 0.2 indicates homozygosity with respect to mutated leptin.

10. The method according to claim 1, wherein the leptin receptor is SEQ ID NO: 10.

11. The method according to claim 7, wherein the quotient, Q, is between 0.9 and 1.1.

12. The method according to claim 7, wherein the quotient, Q, is between 0.3 and 0.7.

13. The method according to claim 7, wherein the quotient, Q, is between 0.4 and 0.6.

14. The method according to claim 7, wherein the quotient, Q, is less than 0.2.

15. The method according to claim 7, wherein the quotient, Q, is less than 0.1.

16. The method according to claim 9, wherein, for the in-vitro diagnosis of obesity, the quotient, Q, between 0.9 and 1.1 indicates homozygosity in the obesity gene with respect to non-mutated leptin.

17. The method according to claim 9, wherein, for the in-vitro diagnosis of obesity, the quotient, Q, between 0.4 and 0.6 indicates heterozygosity in the obesity gene with respect to mutated and non-mutated leptin.

18. The method according to claim 9, wherein, for the in-vitro diagnosis of obesity, the quotient, Q, less than 0.1 indicates homozygosity with respect to mutated leptin.

19. The method according to claim 1, wherein the non-mutated leptin amino acid sequence is SEQ ID NO: 1, and wherein the mutated leptin sequence is selected from the group consisting of SEQ ID NO: 2, SEQ ID NO: 3, SEQ ID NO: 4, and combinations thereof.

* * * * *

UNITED STATES PATENT AND TRADEMARK OFFICE
CERTIFICATE OF CORRECTION

PATENT NO. : 10,175,253 B2
APPLICATION NO. : 15/558322
DATED : January 8, 2019
INVENTOR(S) : Bertram Flehmig Page 1 of 1

It is certified that error appears in the above-identified patent and that said Letters Patent is hereby corrected as shown below:

In the Claims

Column 53, Line 25, Claim 1, delete "L161G, preferably D100Y, N103K and/or L72S, further preferably D100Y;" and insert -- L161G; --

Column 53, Line 37, Claim 1, delete "immunossay" and insert -- immunoassay --

Column 54, Line 32, Claim 11, delete "quotient, Q," and insert -- quotient Q --

Column 54, Line 34, Claim 12, delete "quotient, Q," and insert -- quotient Q --

Column 54, Line 36, Claim 13, delete "quotient, Q," and insert -- quotient Q --

Column 54, Line 38, Claim 14, delete "quotient, Q," and insert -- quotient Q --

Column 54, Line 40, Claim 15, delete "quotient, Q," and insert -- quotient Q --

Column 54, Line 43, Claim 16, delete "quotient, Q," and insert -- quotient Q --

Column 54, Line 47, Claim 17, delete "quotient, Q," and insert -- quotient Q --

Column 54, Line 51, Claim 18, delete "quotient, Q," and insert -- quotient Q --

Signed and Sealed this
Ninth Day of April, 2019

Andrei Iancu
*Director of the United States Patent and Trademark Office*